United States Patent [19]

Summers

[11] Patent Number: 5,395,350
[45] Date of Patent: Mar. 7, 1995

[54] PARACENTESIS VALVE

[76] Inventor: Daniel A. Summers, 5701 Klondike NE., Albuquerque, N. Mex. 87111

[21] Appl. No.: 195,757

[22] Filed: Feb. 14, 1994

[51] Int. Cl.⁶ .......................... A61M 5/00; G05D 7/00
[52] U.S. Cl. .................... 604/249; 137/103; 137/512.3; 417/559; 604/33
[58] Field of Search ............... 604/181, 218, 236, 186, 604/249, 33, 320, 335; 137/102, 103, 512.3, 513.7, 528, 533, 532; 417/559, 569

[56] References Cited

U.S. PATENT DOCUMENTS

| 4,023,588 | 5/1977 | Olander | 137/103 |
|---|---|---|---|
| 4,210,173 | 7/1980 | Choksi et al. | 137/512.3 |
| 4,210,178 | 7/1980 | Morse et al. | 604/249 |
| 4,506,691 | 3/1985 | Tseo | 604/249 |
| 4,782,849 | 11/1988 | Hodge | 137/103 |
| 4,838,866 | 6/1989 | Marshall | 604/236 |

Primary Examiner—John G. Weiss
Attorney, Agent, or Firm—Donovan F. Duggan; Deborah A. Peacock

[57] ABSTRACT

Disclosed is a paracentesis valve apparatus and method of using the valve. The valve comprises a valve body having three apertures and a bypass passageway. A movable valve member with truncated end portions moves linearly within the valve body by means of hydraulic pressure alone. Application of negative hydraulic pressure via a syringe withdraws fluid from a body cavity through the valve into the syringe. Application of positive hydraulic pressure to the syringe pumps the fluid through the valve into a receptacle.

12 Claims, 2 Drawing Sheets

PARACENTESIS VALVE

CROSS-REFERENCE TO RELATED APPLICATIONS

A related application is being filed concurrently herewith, entitled Lavage Valve to Daniel A. Summers, Ser. No. 08/195,926 filed Feb. 14, 1994, and the specification thereof is incorporated herein by reference.

BACKGROUND OF THE INVENTION

1. Field of the Invention (Technical Field)

The invention relates to a paracentesis valve operable solely by hydraulic force; and a method for using such valve.

2. Background Art

The medical procedure known as paracentesis is tedious and potentially dangerous. The procedure normally entails insertion of a syringe or trocar into a body cavity, for example the thoracic or abdominal cavities and subsequent fluid removal or drainage from such cavity.

Paracentesis procedures in the past normally required a manually operated three-way valve. Moving the valve lever in a predetermined direction enabled withdrawal of fluid into a syringe barrel; moving the lever in another direction enabled voiding and expulsion of fluid from the syringe barrel into a receptacle. The disadvantages of this procedure include patient discomfort, improper valve manipulation, valve jamming, and the risk of torn gloves and subsequent infection.

The following U.S. patents are exemplary of the prior art valves and procedure: U.S. Pat. No. 4,844,087 to Garg, entitled First Method for Using Cannula Including a Valve Structure and Associated Instrument Element; U.S. Pat. No. 4,447,235 to Clarke, entitled Thoracentesis Device; U.S. Pat. No. 4,784,156 to Garg, entitled Cannula Including a Valve Structure and Associated Instrument Elements and Method for Using Same; U.S. Pat. No. 4,840,184 to Garg, entitled Second Method for Using Cannula Including a Valve Structure and Associated Instrument Elements; and U.S. Pat. No. 4,832,044 to Garg, entitled Cannula Including a Valve Structure and Associated Instrument Elements.

U.S. Pat. No. 3,957,052, to Topham, entitled Pumping-Syringe, discloses a T-passageway valve configuration for withdrawing and pumping fluids. Ball check valves are used. Similarly, U.S. Pat. No. 4,051,852, to Villari, entitled Aspirating Device, discloses ball, flap and cylindrical check valve member embodiments for withdrawing body fluids and thereafter pumping them into suitable collection bags. U.S. Pat. No. 657,440 to McCaw, entitled Aspirator, discloses similar structure.

U.S. Pat. No. 3,515,163 to Freeman, entitled Respiratory Apparatus does disclose a respiratory valve with a sliding valve member. The sliding valve member, however, is magnetically biased, and flow occurs through centrally located orifices in the sliding valve member. U.S. Pat. No. 3,877,616, to Stevens, entitled Pump With Unitary Valve Member, discloses a reciprocating valve member with upper and lower resilient check valves. U.S. Pat. No. 4,592,382, to Rubin, et al., entitled Anti-Siphon Nozzle, discloses an unbiased slidable valve member.

U.S. Pat. No. 4,246,932, to Raines, entitled Multiple Additive Valve Assembly; and U.S. Pat. No. 4,729,401, to Raines, entitled Aspiration Assembly Having Dual Co-Axial Check Valves, both disclose pumping devices for medical fluids employing resilient disk check valves. U.S. Pat. No. 2,567,391 to Mead, entitled Exhaust Valve Structure also discloses a resilient valve member.

It is seen that none of the above references disclose a biased slidable valve member operable solely by hydraulic force to first withdraw fluid from the patient, then allow such fluid to be automatically voided into a receptacle.

SUMMARY OF THE INVENTION (DISCLOSURE OF THE INVENTION)

In accordance with the present invention there is provided a valve apparatus. The valve apparatus comprises a valve body. The valve body comprises first, second and third orifices and a bypass passageway. The valve apparatus also comprises a valve member comprising first and second end portions. The valve member is movable within the valve body solely by hydraulic pressure.

The valve member also comprises a cylindrical center portion, and the first and second end portion comprises first and second truncated cone end portions. The valve body comprises a hollow central portion complementary in configuration to the valve member. Application of negative hydraulic pressure to the first end portion of the moveable valve member causes fluid flow through the first and second orifices and the bypass passageway while closing the third orifice. Application of positive hydraulic pressure to the first end portion of the valve member causes fluid flow through the first and third orifices while closing the second orifice and the bypass passageway. The bypass passageway comprises an aperture and a pressure relief valve is disposed in the aperture. A check valve is disposed in the aperture. A check valve is disposed in the third orifice.

In accordance with the present invention there is provided a method for using a valve comprising the steps of providing a valve body comprising first, second and third orifices and a bypass passageway; providing a valve member comprising first and second end portions, and moveable in the valve body; and moving the valve member solely by hydraulic pressure. Applying negative hydraulic pressure to the first end of the movable valve member forces fluid through the first and second orifices while closing the third orifice. Applying positive hydraulic pressure to the first end of the movable valve member forces fluid through the first and third orifices while closing the second orifice and the bypass passageway.

A primary object of the present invention is the provision of a hydraulically operated paracentesis valve.

Another object of the invention is the provision of a paracentesis valve which automatically reverses fluid flow.

Yet another object of the invention is the provision of a paracentesis valve which reduces patient discomfort and the possibility of operator error.

Still another object of the invention is the provision of an improved method for paracentesis procedure.

An advantage of the present invention is the elimination of manual manipulation of a three-way paracentesis valve.

Another advantage of the present invention is the lessening of time, effort and fatigue in performing a paracentesis procedure.

Still another advantage of the present invention is the provision of a safe and efficient paracentesis method.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figure 1:
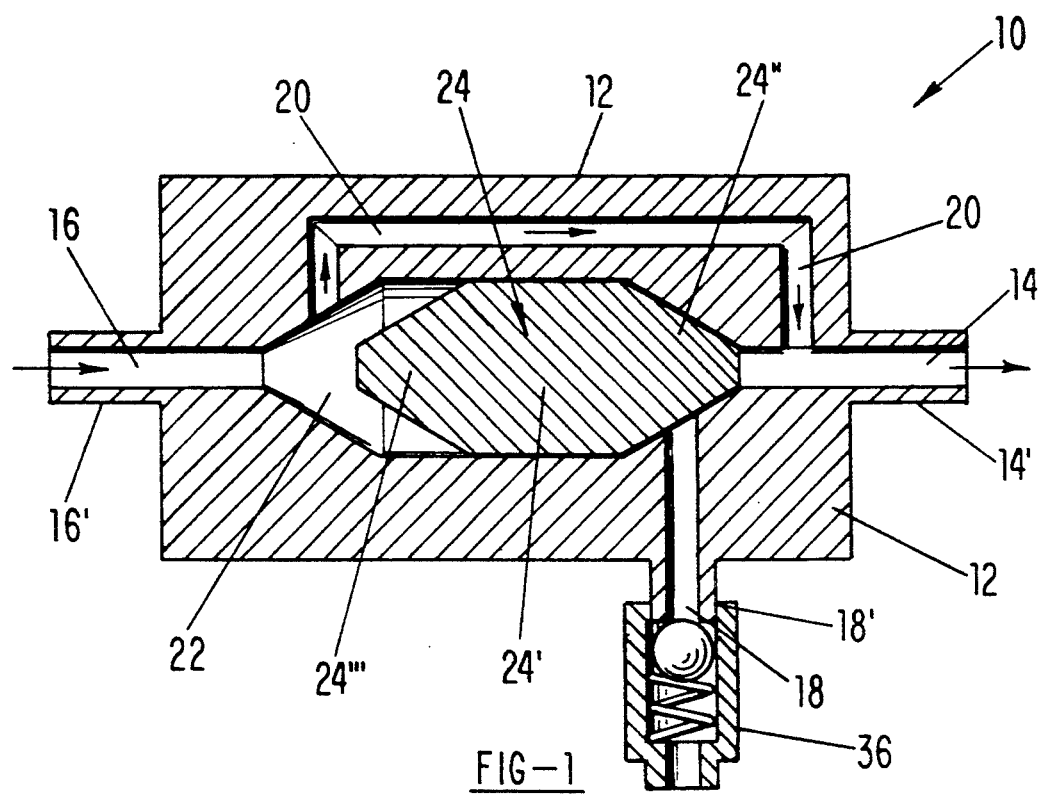
FIG. 1 is a cross-section of the preferred embodiment of the invention with negative hydraulic pressure applied.
Figure 2:
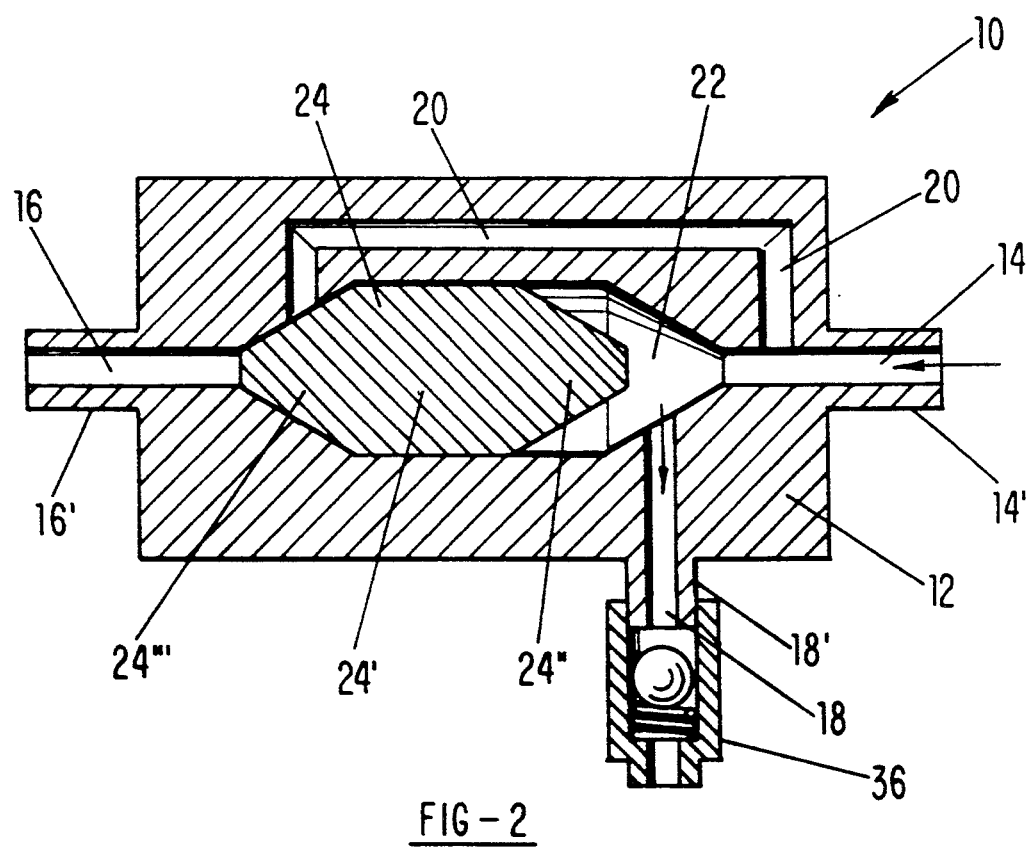
FIG. 2 is a cross-section of the preferred embodiment of the invention with positive hydraulic pressure applied.

Reference is now made to FIGS. 1 and 2 which show the preferred embodiment of the invention. Paracentesis valve 10 comprises valve body 12. Valve body 12 further comprises first, second and third orifices 14, 16 and 18, as well as orifice extensions 14', 16', and 18', respectively. Valve body 12 further comprises bypass passageway 20 which bypasses central cavity 22 and interconnects orifices 14 and 16.

Valve member 24 is positioned within central cavity 22, complementary in configuration to valve member 24 for linear movement therein. Valve member 24, complementary in shape to central cavity 22, comprises cylindrical center portion 24' and truncated cone end portions 24" and 24''', respectively. End portions 24" and 24''' seat within orifices 14 and 16, respectively, of valve body 12, thereby occluding such orifices. Further, when valve member 24 is in position to occlude orifice 14, orifice 18 is also sealed. Concomitantly, orifice 16 and bypass passageway 20 are also simultaneously occluded when valve member 24 is in its leftmost position (see FIG. 2).

Orifice 18 (and orifice extension 18') are coupled to a receptacle or sump (not shown).

Valve 10 may comprise any suitable material compatible with its contemplated medical use. Accordingly, valve 10 may comprise any suitable plastic, stainless steel, aluminum and other such materials known to those ordinarily skilled in the art. If plastics are used, self-lubricating plastics such as nylon or PTFE are preferred in order to facilitate movement of valve member 24 in valve body 12.

Typically, orifice extension 16' is coupled to a hypodermic needle or trocar and cannula for withdrawing fluid from the affected body cavity of the patient. Orifice extension 14' is similarly coupled to a syringe barrel or the like, and is initially empty. Orifice extension 18' is coupled to a receptacle (not shown).

The preferred couplings comprise the well known International Standard Luer conical male or female couplings. In such case, orifice extension 14', 16' and 18' will comprise a 6° taper, and may also comprise the well known "Luer-Loks TM" coupling. Other couplings well known in the art may be employed.

In normal operation, a hypodermic needle or trocar is coupled to orifice extension 16', while an empty syringe is coupled to orifice extension 14'. After insertion of the needle into the body cavity to be drained, the fluid is withdrawn through orifice 14 by manual withdrawal of the syringe piston. The negative hydraulic pressure thereby created moves valve member 24 to the right, as shown in FIG. 1. The entrance to bypass passageway 20 is opened allowing fluid to flow therethrough, as well as through orifices 16 and 14, to the empty syringe. Withdrawal of fluid continues until the syringe barrel is full; at this point, positive pressure is manually applied to the syringe, thereby evacuating the fluid therefrom. As shown in FIG. 2, positive hydraulic pressure moves valve member 24 to the left and fluid then flows through open orifices 14 and 18 to an appropriate receptacle or sump. The paracentesis procedure is repeated until body cavity drainage is considered complete.

Figure 3:
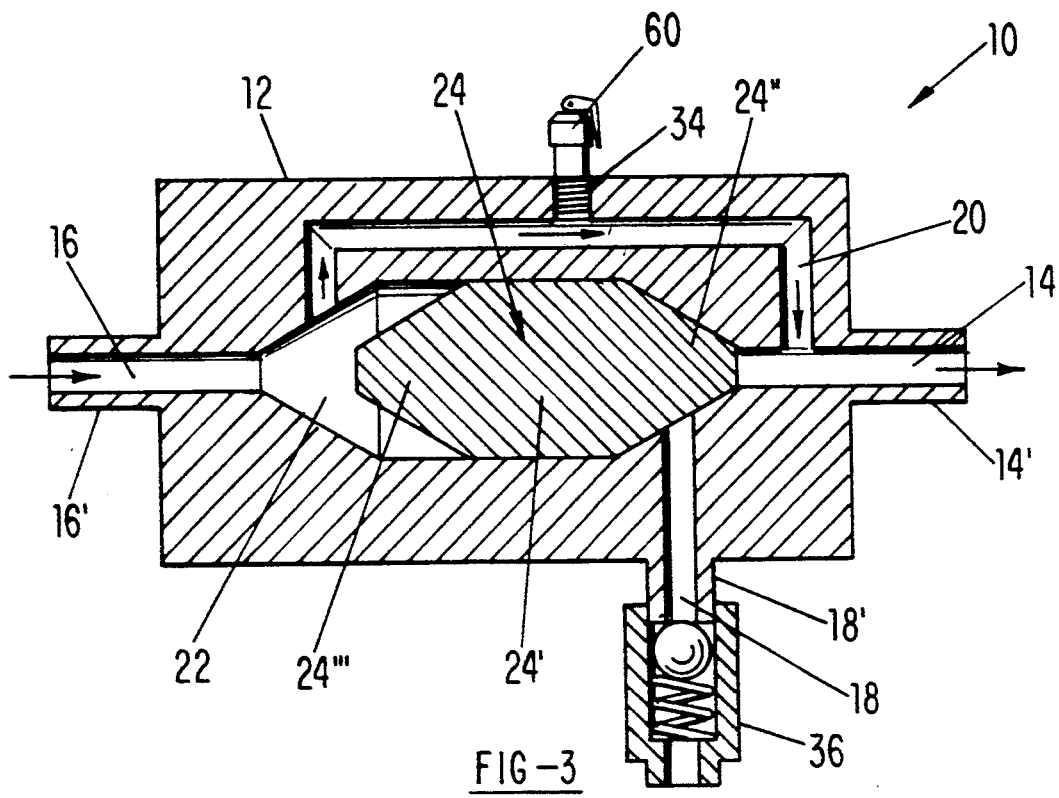
FIG. 3 is a perspective view of a pressure relief valve usable in combination with the preferred embodiment.
Figure 4:
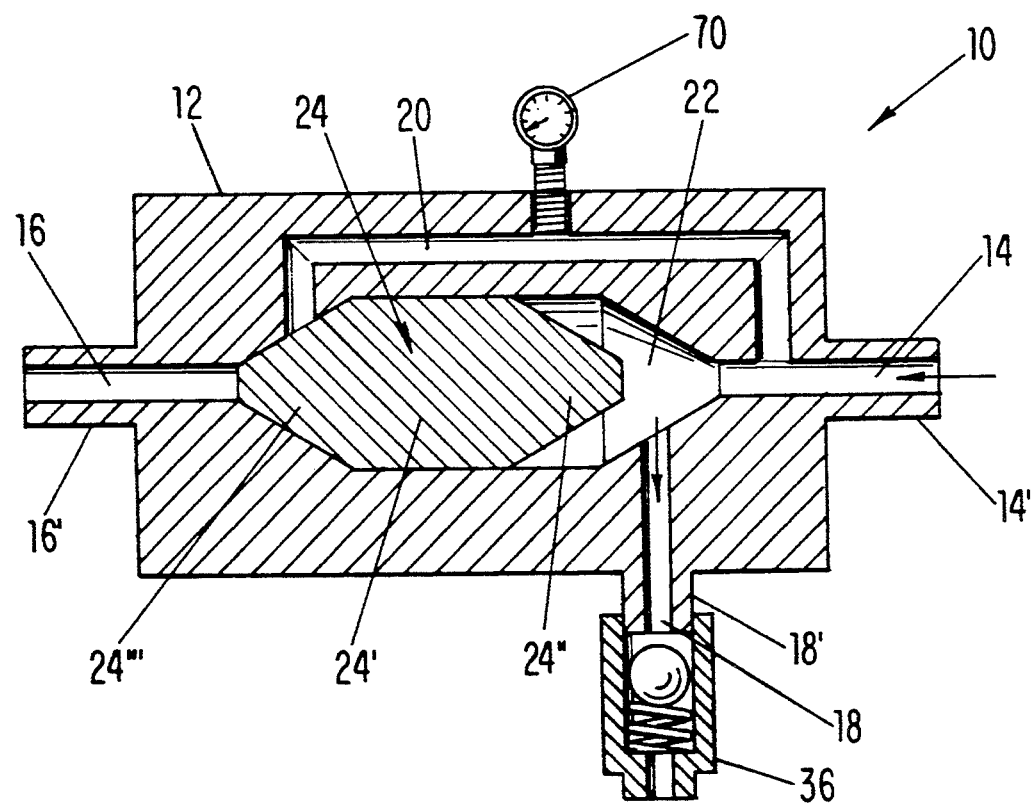
FIG. 4 is a perspective view of a pressure gauge usable in combination with the preferred embodiment.

Another embodiment of the invention is depicted in FIGS. 3 and 4. These embodiments comprises threaded aperture 34 in valve body 12. Threaded aperture 34 provides communication between bypass passageway 20 and the ambient atmosphere, and primarily serves as a training or monitoring device.

FIG. 3 depicts a threaded attachment 60 used in combination with aperture 34. Attachment 60 comprises a "pop off" or pressure relief valve with stem adapted to be screwed or otherwise secured into aperture 34. Pressure relief valve 60 is set to open at a predetermined pressure, for example 21 mm Hg or 20 cm $H_2O$. In operation, medical personnel manually applying pressure to the irrigating syringe would thus be encouraged to apply steady, constant pressure (less than a predetermined pressure) to the irrigating syringe; exceeding the predetermined pressure would open the valve and vent the irrigating fluid.

Similarly, attachment 70 shown in FIG. 4 also serves as a training or monitoring aid. Attachment 70 is a pressure gauge with stem; gauge 70 screws or is otherwise secured into aperture 34, thus affording a visual indication of actual pressure applied to the irrigating syringe. Such visual indication of pressure applied would also tend to encourage steady, uniform application of manual pressure upon the irrigating syringe.

Those skilled in the art will recognize that any known means of securement or attachment may be used to secure valve 60 and gauge 70 in valve body 12, including the threaded means depicted.

In order to ensure that re-injection of fluid does not occur, a simple check valve may be positioned in orifice 18. Such check valve would only permit flow to the receptacle and would preclude flow from the receptacle. The check valve may be of any construction known to the art including, but not limited to ball, flap or cylinder-type valves.

The paracentesis valve of the present invention is useful whenever fluid removal or drainage of a body space is required. It is particularly useful for thoracentesis procedures.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. Valve apparatus comprising:
   a valve body comprising first, second and third orifices and a bypass passageway; and a valve member comprising first and second truncated cone end portions; and said valve member movable within said valve body solely by hydraulic pressure.

2. The invention of claim 1 wherein said valve member comprises cylindrical center portion means.

3. The invention of claim 1 wherein said valve body comprises a hollow central portion complementary in configuration to said valve member.

4. The invention of claim 1 wherein application of negative hydraulic pressure to said first end portion of said moveable valve member causes fluid flow through said first and second orifices and said bypass passageway while closing said third orifice.

5. The invention of claim 1 wherein application of positive hydraulic pressure to said first end portion of said valve member causes fluid flow through said first and third orifices while closing said second orifice and said bypass passageway.

6. The invention of claim 1 wherein bypass passageway comprises an aperture.

7. The invention of claim 6 further comprising a pressure relief valve disposed in said aperture.

8. The invention of claim 6 further comprising a pressure gauge disposed in said aperture.

9. The invention of claim 1 wherein said third orifice comprises a check valve disposed therein.

10. A method for using a valve comprising the steps of:
    providing a valve body comprising first, second and third orifices and a bypass passageway;
    providing a valve member comprising first and second truncated cone end portions, and movable in the valve body; and
    moving the valve member solely by hydraulic pressure.

11. The method of claim 10 comprising the step of applying negative hydraulic pressure to the first end of the movable valve member, thereby forcing fluid through the first and second orifices while closing the third orifice.

12. The invention of claim 10 comprising the step of applying positive hydraulic pressure to the first end of the movable valve member, thereby forcing fluid through the first and third orifices while closing the second orifice and the bypass passageway.

* * * * *